United States Patent

Brooks, Jr.

[11] Patent Number: 5,098,676
[45] Date of Patent: Mar. 24, 1992

[54] STERILIZATION AND STORAGE CONTAINER TRAY

[76] Inventor: John A. Brooks, Jr., 1015 Candia Rd., Manchester, N.H. 03103

[21] Appl. No.: 637,625

[22] Filed: Jan. 4, 1991

[51] Int. Cl.⁵ .............................................. A61L 2/00
[52] U.S. Cl. ................................. 422/292; 422/102; 422/104; 422/297; 206/438; 206/563
[58] Field of Search ............... 422/292, 102, 104, 297, 422/300; 206/363, 370, 438, 439, 562, 563, 564, 565; 15/161, 215, 216, 217, 238

[56] References Cited

U.S. PATENT DOCUMENTS

| 2,604,377 | 7/1952 | Eames | 422/300 |
| 3,697,223 | 10/1972 | Kovalcik et al. | 206/370 |
| 4,485,919 | 12/1984 | Sandel | 206/370 |
| 4,643,303 | 2/1987 | Arp et al. | 206/438 |
| 4,671,943 | 6/1987 | Wahlquist | 206/439 |
| 4,728,504 | 3/1988 | Nichols | 422/297 |
| 4,798,292 | 1/1989 | Hauze | 422/300 |
| 4,915,913 | 4/1990 | Williams et al. | 422/297 |

Primary Examiner—Robert J. Warden
Assistant Examiner—Laura E. Collins
Attorney, Agent, or Firm—Eugene E. Renz, Jr.

[57] ABSTRACT

A mat, sized to fit a sterilization tray, having an upper surface and a lower surface, with a plurality of mat apertures therein in a predetermined pattern. The upper surface has upwardly projecting fingers for supporting surgical instruments above the upper surface, and the lower surface having downwardly projecting feet for supporting the lower surface of the mat above the tray. The tray bottom has a plurality of apertures in a predetermined pattern which are vertically aligned with the mat apertures such that drainage of condensation from the tray is facilitated.

1 Claim, 2 Drawing Sheets

STERILIZATION AND STORAGE CONTAINER TRAY

FIELD OF THE INVENTION

This invention relates to sterile container systems generally, and particularly to container systems for the sterilization and subsequent sterile storage of medical surgical instruments and the like.

BACKGROUND OF THE INVENTION

Sterilization of reusable and delicate, precision surgical instruments and their subsequent sterile storage is of paramount concern to surgeons and hospitals. Sterilized surgical instruments are essential during surgical procedures to minimize the risk of infection.

After sterilization, airborne bacteria may enter sterilization containers through vents and apertures and, if coming in contact with a suitable medium, may incubate to harmful levels. Condensation remaining after sterilization, either in the tray or on the instruments, provides such a medium for the growth of deleterious bacteria during the subsequent storage of the sterilized instruments.

Some example prior art patents which provide for sterilization containers are Arp et al U.S. Pat. No. 4,643,303, Nichols U.S. Pat. No. 4,728,504, and Spence U.S. Pat. No. 4,783,321. These prior art patents generally teach the use of baskets or trays to hold the instruments to be sterilized, and apertures in the baskets which allow for gross drainage of condensation from the baskets to the container floor below the basket. The condensation then must again drain from the container floor. This double drainage increases the risk of condensation remaining in proximity to the sterilized instruments and the subsequent contamination of the condensation by airborne bacteria. These prior art baskets or instrument retention devices are of such design that excessive condensation may be trapped between the instruments and the device.

Many prior art patents have no separate container locking device to provide a sealing effect between the container halves. Thus the flow of steam or other gaseous sterilants during sterilization is not firmly restricted to the apertures. More importantly, air may ingress between the container halves after sterilization, thus increasing the risk of airborne bacterial contamination of any remaining condensation.

U.S. Pat. No. 4,643,303 describes a sterilization container enclosing an instrument basket within a box-like base and cover. The container also includes clamps mounted to the container by hinges for releasably holding the cover to the base. U.S. Pat. No. 4,783,321 describes a sterilization container enclosing an instrument basket within a base and cover. The container also includes a latch mechanism for releasably holding the cover to the base.

Most of the prior art, for example Nichols U.S. Pat. No. 4,728,504, provide for the placement of the instruments on a removable basket or tray which includes apertures formed on the bottom of the tray to allow for the drainage of condensation. The domed configuration of the tray bottom in U.S. Pat. No. 4,728,504 allows for sufficient surface area contact with the instruments such that condensate may be held between the instruments and the tray after sterilization. Such a risk of airborne bacterial contamination of remaining condensation after sterilization increases during increased storage of the sterilized instruments. Thus, it is imperative to remove as much condensation as possible from the container and from the instruments after sterilization.

Hauze, U.S. Pat. No. 4,798,292, describes a non-locking sterilization container with apertures arranged in rows and columns enclosing a flat surfaced insert with apertures arranged in rows and columns such that the apertures in the container and the insert are vertically aligned. Pegs are inserted in the insert apertures to provide horizontal separation of the instruments during sterilization and subsequent presentation of the instruments. The flat surface of the insert and the pegs increase the risk of condensation remaining in proximity to the instruments after sterilization.

This prior art, although providing for condensation drainage, does not sufficiently alleviate the risk of condensation bacterial growth. Condensation may be trapped between the instruments and the excess support surfaces, and condensation may not sufficiently drain from the container due to convoluted drain paths.

It is an object of the present invention to provide a sterilization and storage container tray and mat which substantially reduce the risk of remaining condensation during storage of the instruments.

It is a further object of the present invention to provide a tray surface which provides minimal contact with the instruments to allow for condensation drainage away from the instruments.

It is also an object of the present invention to provide a tray which allows for condensation drainage away from the bottom of the tray.

SUMMARY OF THE INVENTION

It has now been discovered that the objects of the present invention can be accomplished in the following manner. Specifically, an improved sterilization and storage container tray has been discovered which is admirably suitable for minimizing condensation accumulation within the container tray and thus decreasing the risk of condensation bacterial growth.

The container tray consists of two locking tray halves enclosing a mat made of rubber, plastic or other synthetic material suitable for use in sterilization. The mat may be either stiff or flexible, although in the preferred embodiment the mat is made of flexible silicone rubber and is treated to have a low coefficient of friction. The mat includes upwardly tapering finger-like projections on its upper surface upon which the instruments rest. This tapering reduces the total surface contact area between the instruments and the mat and, combined with the low coefficient of friction of the mat, facilitates the gravity drainage of condensation. This smaller total surface contact area also reduces the risk of condensation being trapped between the instrument and the mat.

The mat also has apertures formed on the bottom of the mat through which the condensation drains. The bottom tray base has apertures which correspond to, and are vertically aligned with, the mat apertures so that condensation draining from a mat aperture may pass freely through the corresponding base aperture directly beneath it.

Raised projections are formed on the bottom of the mat to space the mat from the tray bottom so as to further facilitate condensation drainage away from the mat and instruments, thus decreasing the risk of remaining condensation.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 1:
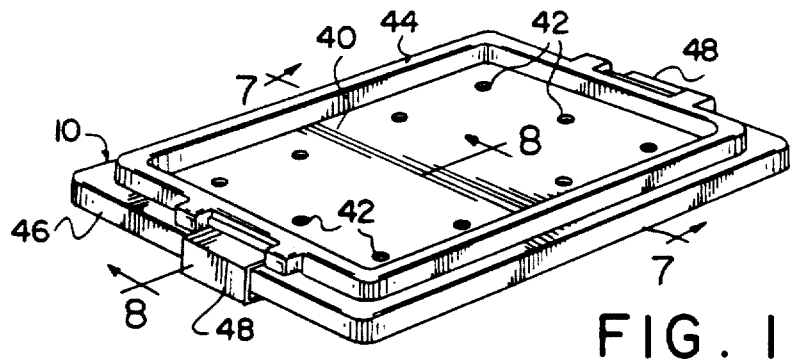
FIG. 1 is a perspective view of the preferred embodiment of the invention showing the invention in the closed and locked position.
Figure 2:
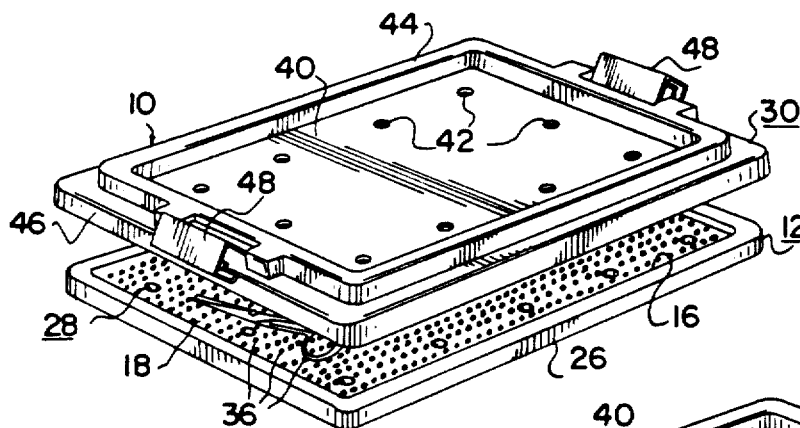
FIG. 2 is a perspective view of the preferred embodiment of the invention of FIG. 1 showing the separation of the tray halves with the mat resting in the bottom tray and with a surgical instrument resting on the mat.
Figure 3:
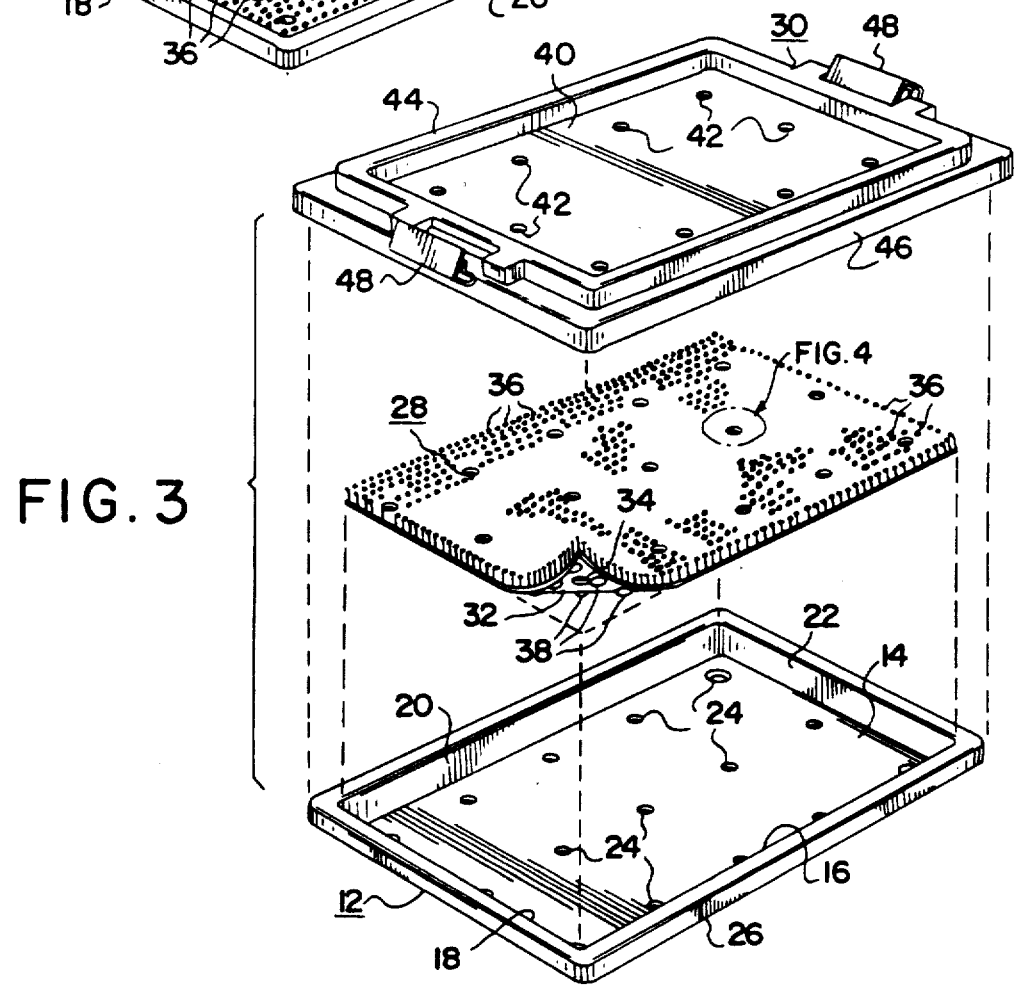
FIG. 3 is a partially exploded view of FIG. 1.

Referring now to the drawings, and to FIGS. 1 and 3, the compact container tray of the present invention is indicated generally by numeral 10 in which surgical instruments may be sterilized, transported and stored for later use. The container tray 10 consists of a box-like base 12 having a bottom 14 and four generally perpendicular upwardly projecting continuous sidewalls comprising a front side wall 16, a left side wall 18, a back side wall 20 and a right side wall 22. The bottom 14 includes a plurality of spaced apertures 24 arranged in a predetermined pattern. Apertures 24 permit ingress and egress of steam or other gaseous sterilants, and allow for condensation drainage. A downwardly projecting lip 26 forms the periphery of base 12.

Figure 5:
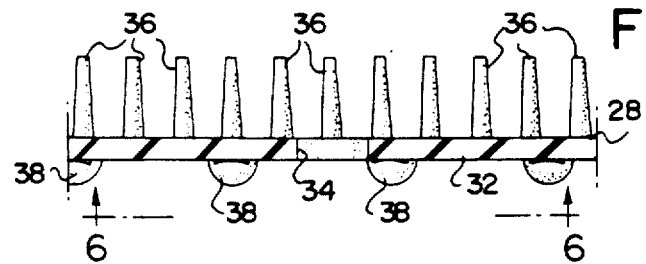
FIG. 5 is a sectional view taken along line 5—5 of FIG. 4.
Figure 7:
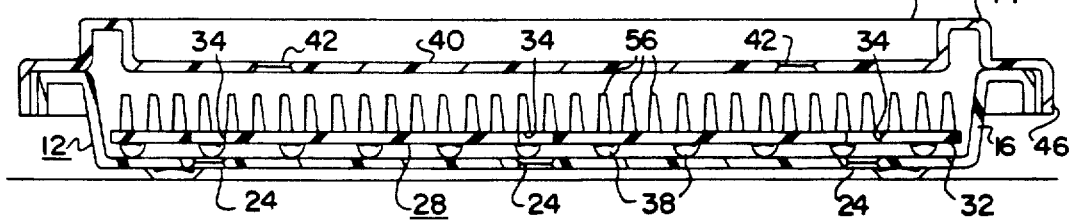
FIG. 7 is an enlarged sectional view taken along line 7—7 of FIG. 1.
Figure 8:
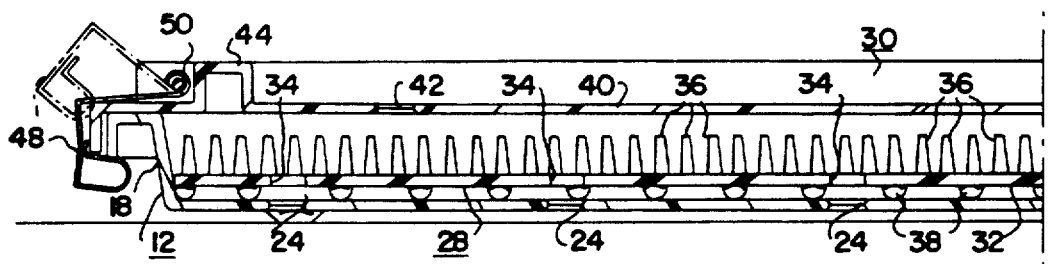
FIG. 8 is a partially sectioned view taken along line 8—8 of FIG. 1.

The support mat 28 is inserted, and rests, within base as shown in FIGS. 2, 3, 7 and 8. The height of the side walls 16, 18, 20, 22 is such that the cover 30 may be placed in a locking position over the base 12 without coming in contact with any surgical instrument placed on the mat 28. See FIGS. 7 and 8. The mat 28 is preferably molded of a heat and moisture resistant silicone rubber, plastic or other synthetic material suitable for use in sterilization. Mat 28 may be treated to reduce its coefficient of friction. As shown in FIGS. 5, 7 and 8, mat 28 includes a flat base section 32 and a plurality of spaced apertures 34 in the base section 32 arranged in a predetermined pattern. The apertures 34 permit the flow of steam or other gaseous sterilants through the base section 32 and are arranged so that each aperture 34 is aligned with a corresponding aperture 24 in the bottom 14 of the base 12. Such alignment of apertures 24 and 34 facilitates the ingress and egress of steam or other gaseous sterilants in relation to the container tray 10. More importantly, this vertical alignment of the apertures 24 and 34 facilitates the drainage of condensation from the mat 28 to the exterior of the container tray 10.

In effect, each pair of corresponding apertures 24, 34 form a shaft through which mat condensation may fall without obstruction to the exterior of the container tray 10. Condensation may drain from the mat 28 through a mat aperture 34 and then directly through the corresponding base aperture 24 directly beneath. Condensation draining from the mat 28 need not fall to the base 12 below and then again drain through a base aperture 24. Instead, mat condensation in effect drains directly from the mat 28 to the exterior of the container tray 10. In combination with the mat 28, this alignment of apertures 24, 34 further reduces the risk of remaining condensation.

Turning now to FIGS. 4-8, the base section 32 of the mat 28 has a plurality of support fingers 36 arranged in a predetermined pattern and extending upwardly from the base section 32. Each finger 36 tapers upwardly from its base and functions to support surgical instruments of varying sizes and weights. The tapering of the fingers 36 as shown in FIG. 5 facilitates the drainage of condensations down and away from the surgical instruments.

The base section 32 of the mat 28 also has a plurality of rounded feet 38 extending downwardly from the base section 32. The feet 38 support the mat 28 and space the base section 32 above the bottom surface 14 of the base 12. Steam and other gaseous sterilants may freely pass underneath the mat 28 during sterilization and condensation may then freely drain away from the mat 28 and through the apertures 24.

Figure 4:
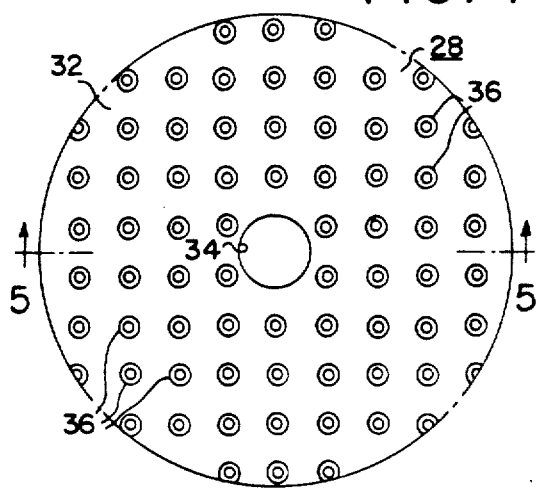
FIG. 4 is an enlarged overhead plan view of the circle designated "FIG. 4" of FIG. 3.
Figure 6:
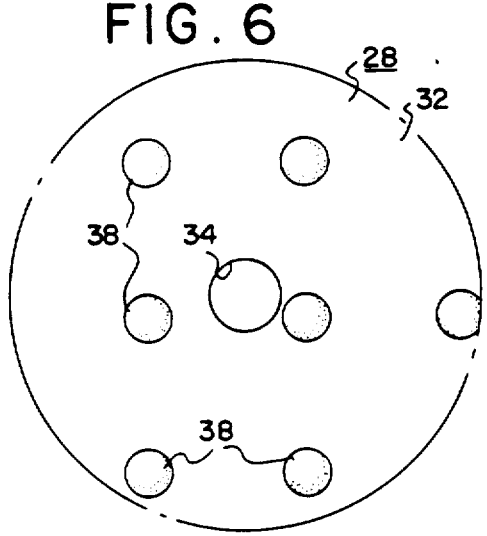
FIG. 6 is a bottom plan view taken along line 6—6 of FIG. 5.

FIGS. 4 and 6 show the obverse and reverse of the mat 28 and demonstrate the arrangement and relative number and size of the fingers 36 and feet 38, respectively. The support mat 28 may be molded from rubber and provides an economical and easily replaceable support structure for surgical instruments during sterilization, transport and storage. The mat 28 may also be molded as a large sheet and then custom cut to fit sterilization enclosures of varying shapes and sizes and allows for economical and efficient replacement of such mats.

As shown in FIGS. 1-3, 7 and 8, cover 30 is of a box-like shape and includes a top surface 40 with a plurality of spaced apertures 42 arranged about the periphery of the top surface 40 which permit the ingress and egress of steam and other gaseous sterilants during sterilization, and the drainage of condensation from the top surface 40. The cover 30 also includes a rectangular raised ridge section 44 which surrounds and defines the top surface 40, and a downwardly projecting lip section 46 which engages the lip section 26 of the base 12 to provide a sealing contact between the lip sections 26, 46 when the cover 30 is locked upon the base 12. This sealing contact causes the steam or other gaseous sterilants to ingress and egress the container tray 10 only through the apertures 24, 42.

The cover 30 also includes locking hinges 48 made of a flexible metal or plastic which are attached to the cover 30 by hinge pins 50 at the midway position on opposite ends of the cover 30 as shown in FIGS. 1-3, and 8. As shown in FIG. 8, the locking hinges 48 pivot about hinge pins 50 between a locking and a non-locking position.

While particular embodiments of the present invention have been illustrated and described herein, it is not intended to limit the invention and changes and modifications may be made thereon within the scope of the following claims.

What is claimed is:

1. A sterilization tray assembly for sterilizing, transporting, and storing instruments, comprising:
   a tray, having:

an upper tray section including a plurality of upper tray ports spaced in a predetermined pattern;

a lower tray section including a plurality of lower tray ports spaced in a predetermined pattern;

locking means for engaging said upper tray section and said lower tray section to form a sealing contact between said tray sections; and a mat made of silicone rubber and sized to fit said tray, said mat being positioned between said tray sections and having an upper surface and a lower surface, said mat including;

a plurality of mat ports in said mat spaced in a predetermined pattern wherein said mat ports and said lower tray ports are in vertical alignment;

a plurality of upwardly tapered, vertical projections spaced in a predetermined pattern on said upper surface, said vertical projections having tips at their free ends to provide support for instruments above said upper surface;

a plurality of downwardly projecting support feet depending from said lower surface spaced in a predetermined pattern for spacing said lower surface above said lower tray section.

* * * * *

REEXAMINATION CERTIFICATE (2992th)
United States Patent
Brooks, Jr.

[11] B1 5,098,676
[45] Certificate Issued Sep. 10, 1996

[54] STERILIZATION AND STORAGE CONTAINER TRAY

[75] Inventor: John A. Brooks, Jr., Manchester, N.H.

[73] Assignee: Poly-Vac, Inc., Manchester, N.H.

Reexamination Request:
No. 90/004,187, Mar. 20, 1996

Reexamination Certificate for:
Patent No.: 5,098,676
Issued: Mar. 24, 1992
Appl. No.: 637,625
Filed: Jan. 4, 1991

[51] Int. Cl.⁶ .................................................. A61L 2/00
[52] U.S. Cl. .................... 422/292; 422/102; 422/104; 422/297; 206/438; 206/563
[58] Field of Search .................. 422/292, 102, 422/104, 297, 300; 206/363, 370, 438, 439, 562, 563, 564, 565; 15/161, 215, 216, 217, 238

[56] References Cited

U.S. PATENT DOCUMENTS

| | | | |
|---|---|---|---|
| 2,604,377 | 7/1952 | Eames | 21/61 |
| 3,697,223 | 10/1972 | Kovalcik et al. | 21/83 |
| 4,485,919 | 12/1984 | Sandel | 206/370 |
| 4,643,303 | 2/1987 | Arp et al. | 206/370 |
| 4,671,943 | 6/1987 | Wahlquist | 422/300 |
| 4,728,504 | 3/1988 | Nichols | 422/297 |
| 4,783,321 | 11/1988 | Spence | 432/300 |
| 4,798,292 | 1/1989 | Hauze | 206/439 |
| 4,915,913 | 4/1990 | Williams et al. | 422/119 |

OTHER PUBLICATIONS

Brochure from Katena Products Inc., "The Katena Eye Opener," copyright 1986.
1989 Ad for Poly Vac Silicone Nipple Mat System and Custom Formed Containers.

*Primary Examiner*—Laura E. Edwards

[57] ABSTRACT

A mat, sized to fit a sterilization tray, having an upper surface and a lower surface, with a plurality of mat apertures therein in a predetermined pattern. The upper surface has upwardly projecting fingers for supporting surgical instruments above the upper surface, and the lower surface having downwardly projecting feet for supporting the lower surface of the mat above the tray. The tray bottom has a plurality of apertures in a predetermind pattern which are vertically aligned with the mat apertures such that drainage of condensation from the tray is facilitated.

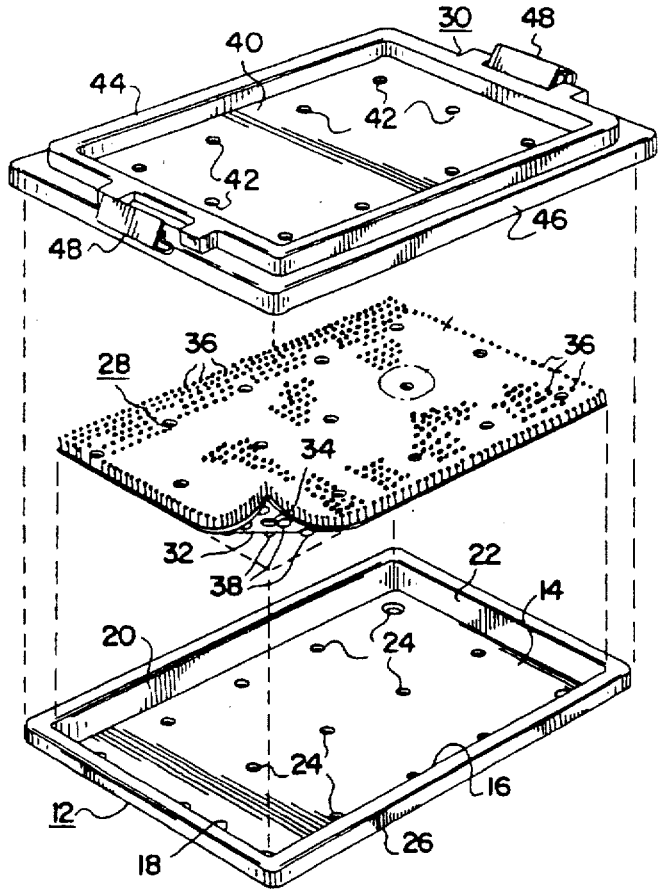

B1 5,098,676

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

1. A sterilization tray assembly for sterilizing, transporting, and storing instruments, comprising:
   a tray, having;
      an upper tray section including a plurality of upper tray ports spaced in a predetermined pattern;
      a lower tray section including a plurality of lower tray ports spaced in a predetermined pattern;
      locking means for engaging said upper tray section and said lower tray section to form a sealing contact between said tray sections; and
   a *flexible* mat made of silicone rubber and sized to fit said tray, said mat being positioned between said tray sections and having an upper surface and a lower surface, said mat including;
      a plurality of mat ports in said mat spaced in a predetermined pattern wherein said mat ports and said lower tray ports are in vertical alignment;
      a plurality of upwardly tapered, vertical projections spaced in a predetermined pattern on said upper surface, said vertical projections having tips at their free ends to provide support for instruments above said upper surface;
      a plurality of downwardly projecting support feet depending from said lower surface spaced in a predetermined pattern for spacing said lower surface above said lower tray section.

* * * * *